(12) United States Patent
Miller et al.

(10) Patent No.: US 6,267,017 B1
(45) Date of Patent: Jul. 31, 2001

(54) TWO-DIMENSIONAL ARRAY FOR ELECTROMECHANICAL AND ELECTROCHEMICAL SPECTROSCOPY

(75) Inventors: Michael A. Miller; Stephen J. Hudak, Jr., both of San Antonio, TX (US)

(73) Assignee: Southwest Research Institute, San Antonio, TX (US)

(*) Notice: Subject to any disclaimer, the term of this patent is extended or adjusted under 35 U.S.C. 154(b) by 0 days.

(21) Appl. No.: 09/633,946

(22) Filed: Aug. 8, 2000

Related U.S. Application Data (62) Division of application No. 09/115,114, filed on Jul. 14, 1998.

(51) Int. Cl.⁷ .................................................. G01N 33/00
(52) U.S. Cl. ........................................................... 73/866
(58) Field of Search .............................. 73/767, 772, 794, 73/808, 862.046, 866

(56) References Cited

U.S. PATENT DOCUMENTS

| | | | |
|---|---|---|---|
| 4,133,722 | | 1/1979 | Ensanian ............................ 205/790.5 |
| 4,864,329 | * | 9/1989 | Kneezel et al. ....................... 364/140 |
| 5,006,786 | | 4/1991 | McKubre et al. ................. 205/790.5 |
| 5,419,201 | | 5/1995 | Li et al. .................................. 73/808 |
| 5,491,408 | | 2/1996 | Rousseau ............................ 324/71.1 |
| 5,560,811 | * | 10/1996 | Briggs et al. ......................... 204/451 |
| 5,650,058 | * | 7/1997 | Wenske et al. ....................... 205/615 |
| 5,859,537 | | 1/1999 | Davis et al. .......................... 324/693 |
| 6,151,969 | * | 11/2000 | Miller et al. ........................... 73/808 |

* cited by examiner

Primary Examiner—Max Noori
(74) Attorney, Agent, or Firm—Baker Botts L.L.P.

(57) ABSTRACT

A transducer cell array for electrochemical and electromechanical spectroscopy testing. The array has rows and columns of electrolytic volume cell elements that are spatially uniform. A reference electrode is common to all volume elements. Each counter electrode is individually addressable. The total impedance response provides a spatial image of the surface being tested.

8 Claims, 12 Drawing Sheets

- ●- OCP; 7075 Al
- ▲- OCP; 7075 Al
- ■- CONST. POLARIZATION; 7075 Al

TWO-DIMENSIONAL ARRAY FOR ELECTROMECHANICAL AND ELECTROCHEMICAL SPECTROSCOPY

RELATED APPLICATIONS

This application is a divisional of U.S. application Ser. No. 09/115,114, filed Jul. 14, 1998, by Michael A. Miller and Stephan J. Hudak, and entitled ELECTROMECHANICAL AND ELECTROCHEMICAL IMPEDANCE SPECTROSCOPY FOR MEASURING AND IMAGING FATIGUE DAMAGE.

GOVERNMENTAL RIGHTS

The U.S. Government has a paid-up license in this invention and the right in limited circumstances to require the patent owner to license others on reasonable terms as provided for by the terms of U.S. Government Contract No. F41608-96-D-0108-010 awarded by the United States Air Force.

TECHNICAL FIELD OF THE INVENTION

This invention relates to non-destructive testing of materials for their fatigue status, and more particularly to a transducer cell array for use with electrochemical and electromechanical impedance methods for such testing.

BACKGROUND OF THE INVENTION

Fatigue damage of various materials has been a topic of considerable economic importance and one to which a significant amount of scientific and engineering effort has been devoted over the latter half of this century. Methods for non-destructive testing are of particular interest.

Fatigue damage is intimately tied to microscopic structural and chemical processes that occur at the points of microdeformations, which develop over time as a material is strained. These processes have been used advantageously as the basis of analytical techniques that measure fatigue damage within metallic materials under simulated service conditions. For example, under conditions of applied cyclic deformation, chemical processes such as the oxidation, leading to passive film formation, and reoxidation, subsequent to passive film rupture, of a metal substrate at points of microdeformation can be probed electrochemically.

Electrochemical fatigue measurement is the subject of U.S. Pat. No. 5,419,201, entitled "Methods and Devices for Electrochemically Determining Metal Fatigue Status", to Li and Laird. This measurement technique uses a three-electrode electrolyte-filled cell to provide an elecrochemical interface with the material under test. The material is subjected to cyclic mechanical deformations, and during these deformations, the transient current passing through the electrolyte are measured. The current's signature is analyzed to determine the fatigue status of the material.

Another electrochemical technique that has recently been studied is that of electrochemical impedance spectroscopy. "Impedance", in its most general sense, can be the quotient of any cyclic input perturbation (e.g., mechanical, electrical or optical) and a consequent cyclic output response. A "true" electrical impedance is measured by applying an ac voltage to the material, measuring the response current and phase relationship, and calculating the impedance ($Z=V/I$). An electrolyte-filled cell having two or three electrodes is used to apply the input voltage and to measure the output current. Impedance values over a suitable spectrum of frequencies can be related to physical and chemical properties of the material.

SUMMARY OF THE INVENTION

One aspect of the invention is a transducer cell array for use in materials testing, such as electromechanical or electrochemical spectroscopy. The array has a number of array layers. A capillary layer has a number of on-conductive capillary elements open at each end. A bottom end of each capillary element may be placed on the surface of a material under test. An electrically conductive reference electrode layer is placed at the upper surface of the capillary array. This reference electrode layer extends down into at least a portion of each capillary element, thereby forming a reference electrode for each capillary element. A contact point array layer is above the reference electrode layer. It has a number of electrically conductive contact points. Each contact point forms a counter electrode for a corresponding capillary element. A contact grid has a number of electrical leads, one lead corresponding to each counter electrode, such that each counter electrode is individually addressable.

DETAILED DESCRIPTION OF THE INVENTION

The invention described herein relates to both electrochemical and electromechanical impedance spectroscopy to detect and analyze fatigue damage to a material. The "fatigue damage" may be prior to or after crack initiation. "Fatigue damage" includes damage associated with aggressive environments such as corrosion-fatigue or stress-corrosion-cracking due to the presence of chemical species, or creep-fatigue due to the presence of elevated temperature.

The invention involves a distinction between electrochemical impedance spectroscopy (EIS) and electromechanical impedance spectroscopy (EMIS), and a recognition that both methods may be performed together or they may be performed independently of each other. As explained more completely below, EIS measures the relaxational current or voltage response of a material to a current or voltage perturbation. In EMIS, the perturbation is a cyclic mechanical load and the response of the system is measured as current or voltage. Both EMIS and EIS can be used to obtain a transfer function corresponding to a frequency-dependent impedance.

Single-Element Electrochemical Transducer Cell

Figure 1A:
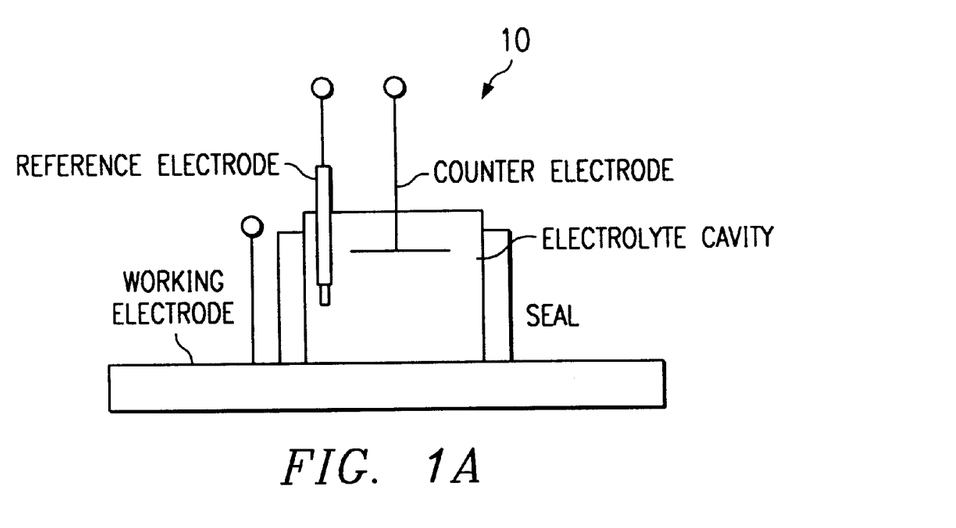
FIG. 1A illustrates a conventional electrochemical transducer cell used for various electrochemistry applications.

FIG. 1A illustrates a conventional electrochemical transducer cell 10 used for various electrochemistry applications. This same cell 10 may be used for impedance analysis (both EIS and EMIS) in accordance with the invention. Cell 10 is filled with an electrolyte and contains three electrodes. The material under test constitutes a working electrode. A seal is used to place the cell 10 against the material under test and to isolate it from the remaining environment. The material under test is thus exposed to the electrolyte and is maintained at a desired potential with respect to a reference electrode. The counter electrode is made from an inert metallic material and is held at whatever voltage is required to maintain a desired potential between the working electrode and the reference electrode.

Figure 1B:
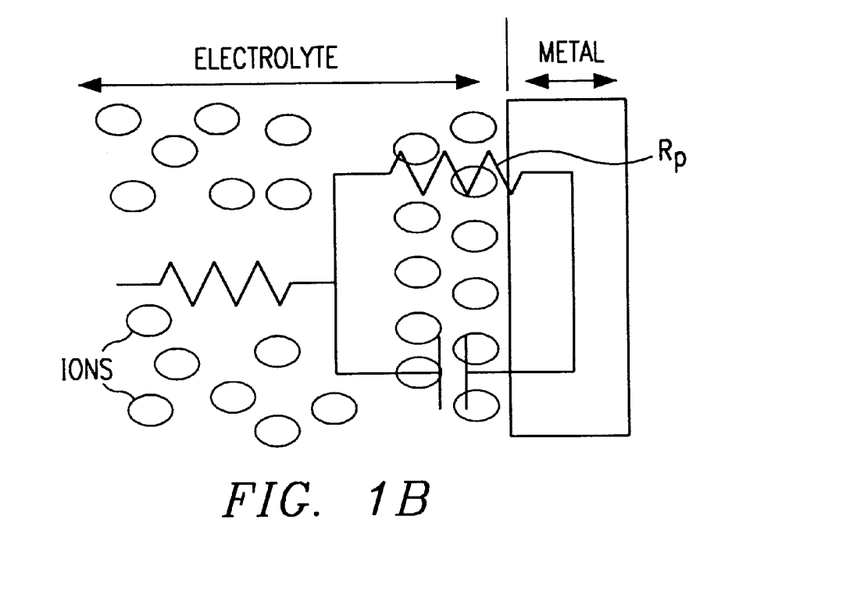
FIG. 1B illustrates an electrical circuit model of the interface between the electrolyte within the transducer cell and the material being tested.

FIG. 1B illustrates an electrical circuit model of the interface between the electrolyte within cell 10 and the material being tested. The electrolyte provides a fluid contact with the surface of the material, contacting the entire surface regardless of irregularities. Ions at the interface of the electrolyte and the material under test form the parallel resistor/capacitor combination. The bulk of the electrolyte acts like a resistor.

EIS/EMIS Instrumentation

Figure 2:
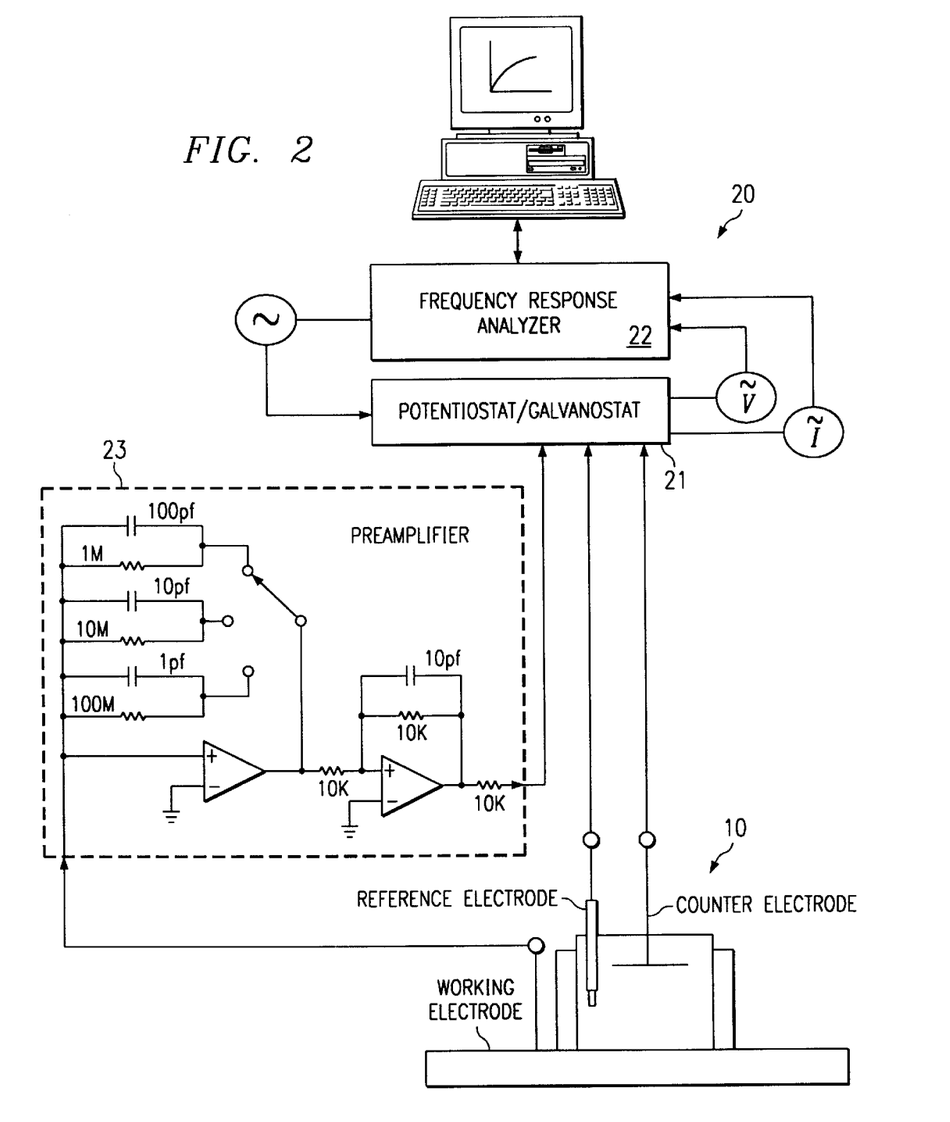
FIG. 2 illustrates a fatigue measurement system in accordance with the invention.

FIG. 2 illustrates a fatigue measurement system 20 in accordance with the invention. The use of a three-electrode cell 10 is consistent with conventional electrochemical materials analysis and permits control over the polarization potential within the cell. However, cell 10 might also be a two-electrode cell (no reference electrode). In this case, system 20 would be used in a galvanostatic rather than potentiostatic mode.

A control/meter unit 21 has means for both controlling the potential applied to cell 10 and for measuring the cell current and cell voltage. Control/meter unit 21 may be implemented with conventional potentiostat and galvanostat circuitry. The potential control permits electrochemical changes in the material under test to be controlled. For example, the material may be passivated in the sense that a surface oxide is formed so as to prevent further oxidation.

An impedance measurement unit 22 receives the voltage and current values from the control unit 21.

There are a variety of implementations of impedance measurement unit 22, such as a frequency response analyzer or phase-sensitive detector (lock-in amplifier).

A preamplifier 23 may be used in-line with the working electrode input lead from the transducer cell 10 to the control/meter unit 21. Pre-amplification may be desirable when the electrodes are small or when chemical electron transfer processes are not a significant contribution to the measured current response.

As in FIG. 1A, the working electrode is the material under test. The material under test may be a metal, metal alloy, polymer, polymeric composite, or semiconductor. It may be a coating over a substrate, with either the coating or the substrate comprising any of these materials. As explained below, the method of the invention is not reliant on corrosion currents to obtain measurement data. The material under test need not be metallic, but need only be at least somewhat conductive.

In operation for obtaining EMIS data, the material under test is mechanically perturbed. This may be accomplished by known means of applying strain (not shown), such as the fatigue machine described below in connection with Examples 1–3.

Also, in operation for obtaining EIS data, the material under test is electrically perturbed. To this end, control unit 21 may apply a sinusoidal electrical perturbation signal to the working electrode (the material under test). As explained below, this is a low amplitude signal and is stepped through a range of frequencies to obtain impedance spectrum data. In other embodiments, impedance spectrum data could be obtained by applying a white noise voltage perturbation signal and using appropriate Fourier analysis to obtain the spectrum data.

Impedance Analysis

The method of the invention measures the response of a material to frequency-varying perturbations of mechanical and/or electrical origin. A transfer function (i.e., output response signal over input perturbation signal) can be defined for each case.

A total impedance response of a material undergoing both mechanical and electrical perturbations can be generalized by the following total impedance function:

$$Z(j\omega'; j\omega'') = Z_\sigma(j\omega') + \sum_n Z_{E,n}(j\omega'') \tag{1}$$

The first term, $Z_\sigma(j\omega')$, is the frequency-dependent impedance associated with cyclic mechanical perturbations of frequency $\omega'$, i.e., the electromechanical impedance (EMIS). The EMIS contribution to the total impedance function is an impedance of current output versus cyclic mechanical load input. The EMIS contribution may also be measured as a "true" electrical impedance where the input perturbations are measured as voltage perturbations in cell 10 that are induced by mechanical perturbations. In either case, the material is mechanically perturbed.

The second term is a linear combination of n frequency-dependent complex impedances associated with cyclic electrical perturbations of frequency $\omega''$ of a material comprising n material component interfaces, i.e., the electrochemical impedance (EIS). For example, in the case of a coated substrate, the electrolyte-coating interface, and the coating-substrate interface constitute two components.

Figure 3A:
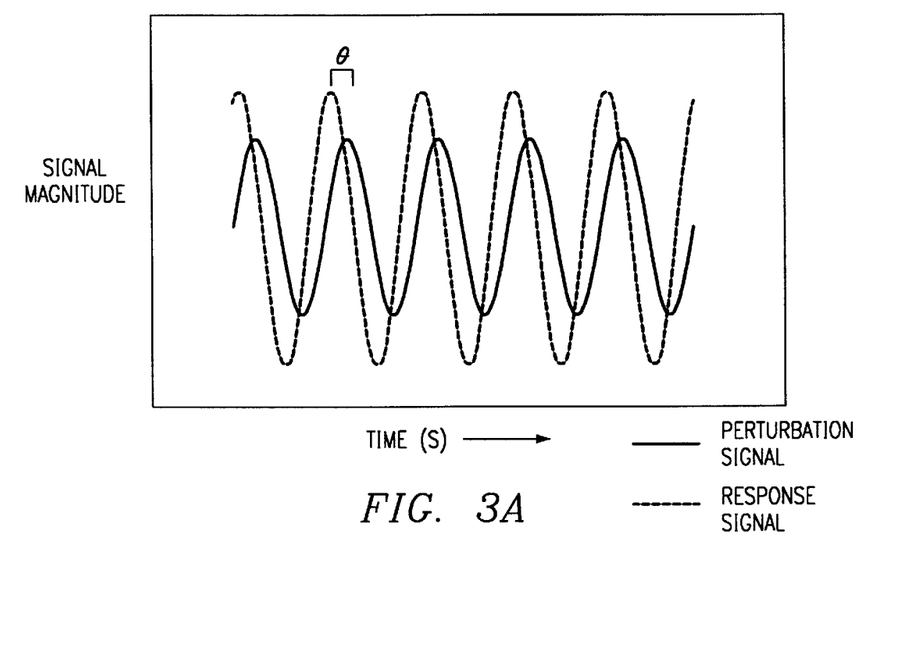
FIG. 3A illustrates the analog perturbation/response relationship of EMIS and EIS.
Figure 3B:
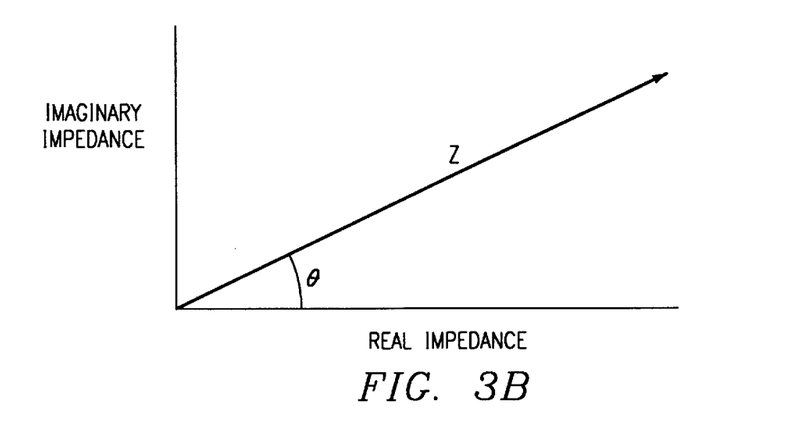
FIG. 3B illustrates the impedance resulting from the relationship of FIG. 3A.

FIGS. 3A and 3B are graphical representations of the perturbation/response relationship of EMIS and EIS.

Specifically, FIG. 3A illustrates the analog perturbation and response signals. As discussed above, the perturbation may be represented by an EMIS signal (representing a mechanical perturbation, $\sigma(j\omega)$, or mechanically-induced voltage perturbation, $V_\sigma(j\omega)$) or by an EIS signal (representing voltage perturbation, $V(j\omega)$). The phase relationship between the perturbation signal and the response current, $I(j\omega)$, is indicated as $\theta$. FIG. 3B illustrates the impedance, $Z=\sigma/I$ or $Z=V/I$, that results from the relationship of FIG. 3A. In other words, the phase angle of FIG. 3A defines a vector, Z, which represents impedance having both real and imaginary terms, and whose length is dependant on the frequency of the perturbation.

For simple electrolyte/material interfaces having a single time constant, the EIS impedance term may behave in accordance with a single impedance arc, described as follows:

$$Z_E(j\omega'') = Z_{E,\infty} + \frac{Z_{E,0} - Z_{E,\infty}}{1 + (j\omega''\tau)^\beta} \quad (2)$$

where the subscripts $\infty$ and 0 denote the high-and low frequency limits of the impedance, respectively. The parameter $\beta$ takes into consideration non-ideal behavior of the system whereby individual processes are governed by a distribution of relaxation times or a distribution of activation energies. The above mathematical representation of the impedance arc, is referred to as a Cole-Cole distribution model.

A practical implication of the total impedance function is that the application of mechanical perturbations is important only to the EMIS term. These mechanical perturbations may be either experimentally controlled or occur inherently within the field environment. Experimental control of mechanical perturbations is ordinarily relegated to a laboratory environment rather than the field environment. In the field environment, mechanical perturbations exist as the mechanical spectrum loading of the system whose Fourier components have multiple frequencies and amplitudes that transform into a unique electromechanical impedance response. Appropriate Fourier analysis may be used to interpret this response.

The EMIS and EIS terms of the total impedance function may be measured and analyzed independently of each other. In other words, in the absence of cyclic mechanical strain and with applied electrical perturbations, the total impedance function reduces to an EIS measurement. The electrical perturbations may be applied as a voltage sinusoid, and the current response measured. The phase difference between the input voltage and output current represents a true electrical impedance. These measurements are taken for a range of discrete frequencies. Analysis of the EIS term of the total impedance function requires only an appropriate spectrum of electrical perturbations, without the need for mechanical perturbations. As an alternative to a voltage perturbation, a current perturbation may be applied, and the resulting voltage measured. For purposes of the claimed invention, the use of current input and voltage output signals is equivalent to the use of voltage input and current output signals. Also, as an alternative to electrical perturbations applied over a range of discrete frequencies, white-noise electrical perturbations may be applied, and an appropriate Fourier analysis used to deconvolve the impedance spectrum.

The following Examples 1–3 are of EIS methodology used to obtain EIS impedance data. The measurements are of a cyclic voltage perturbation and the corresponding cyclic current response. It should be understood that equivalent data could be obtained with input current perturbation signals and output voltage response signals. Also, similar data could be obtained with EMIS methodology, using input mechanical perturbations and output current or voltage response signals.

In each example, the overall objective of the EIS method is to measure the response of an electrochemically active system to an applied frequency-varying perturbation under a carefully controlled polarization potential (constant DC or open circuit). The perturbations are generally low amplitude to provide measurement data within a generally linear range, but the amplitude may vary under different test conditions. For example, a coated material might require perturbations of higher amplitude to provide an suitable response signal.

A transfer function (i.e., output over input) in terms of impedance can be defined for the relaxational processes that are inherent to the electrochemical system. The phase relationship between the input perturbation and output response is frequency dependent. The transfer function corresponds to a true electrical impedance, $Z(\omega)=E/I$.

EXAMPLE 1

For Example 1, the EIS method of the present invention was used to determine fatigue damage within a rod-shaped specimen of aircraft aluminum alloy (7075 Al). To simulate fatigue such as the test material might actually undergo during use, a mechanical fatigue machine was used. The fatigue machine was configured so that EIS measurements could be performed without having to remove the specimen from the fatigue machine. The system of FIG. 2 was used to measure the electrochemical impedance spectrum of the specimen at discrete intervals of the specimen's fatigue life.

More specifically, the fatigue machine (Model MTS, 10 kip capacity) was employed to impart progressive states of fatigue damage by subjecting the specimen to fully reversed (R=−1) sinusoidal mechanical loads at a peak stress of 50 ksi and frequency of 1 Hz. The specimen was mechanically fatigued under these conditions over a series of fatigue cycles until failure was achieved. During the fatigue cycles, the specimen was subjected to the open circuit potential (OCP) of electrochemical transducer cell 10.

At the end of each fatigue cycle in the series, during a measurement interval wherein the specimen experienced neither mechanical perturbations or constant loading, the electrochemical impedance spectrum of the specimen was measured over discrete frequencies of small amplitude (8–12 mV) electrical voltage perturbations spanning 100 KHz to 50 MHZ. These voltage perturbations were centered around a DC polarization potential of +300 mV versus the reference electrode (a saturated calomel electrode). This polarization potential in combination with the electrolyte was determined previously to be well within the steady-state passive region of the aluminum alloy. The liquid electrolyte consisted of 0.3 M $H_3BO_3$+0.075 M $Na_2B_4O_7$+0.06 M $Na_2MoO_4$ in water with a final pH of 8.4.

Figure 4A:
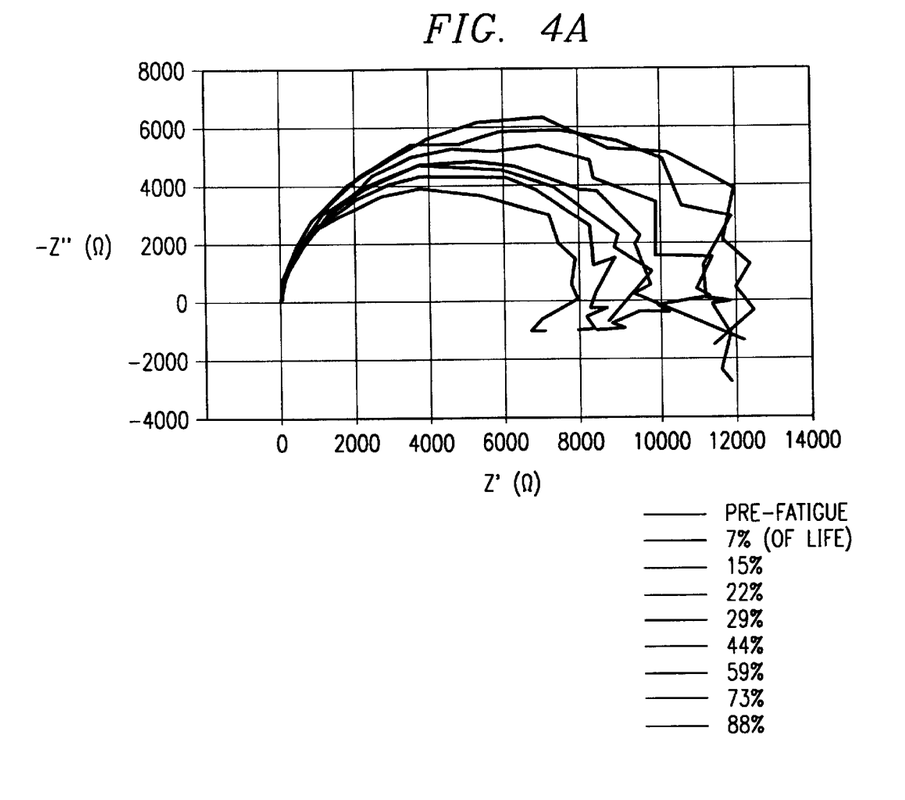
FIG. 4A is a Nyquist plot of the electrochemical impedance responses of an aircraft aluminum alloy during progressive states of mechanical fatigue damage, where the electrochemical transducer cell is held at open circuit potential.

FIG. 4A is a Nyquist plot of the electrochemical impedance responses of the aircraft aluminum alloy during progressive states of mechanical fatigue damage. The real (R) and imaginary (jX) terms of the impedance spectrum are plotted against each other, where $Z=R+jX$. At each fatigue state of the material, the impedance data forms an "impedance arc", which is described mathematically above. This single time constant impedance response has an inductive characteristic at low frequencies.

For each impedance arc, frequency decreases in the clockwise direction. There is a monotonic contraction of the impedance arcs as the specimen accumulates progressively greater amounts of fatigue damage.

Figure 4B:
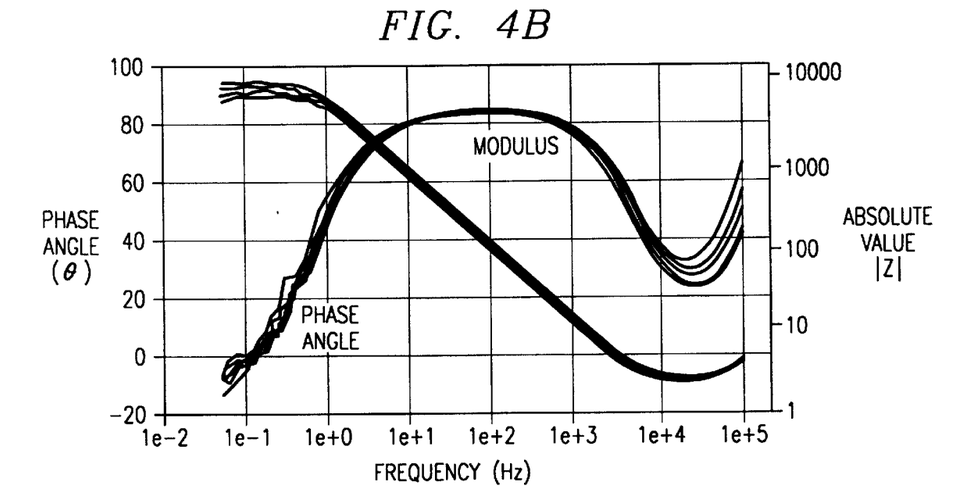
FIG. 4B is a Bode plot of the impedance data of FIG. 4A, where the phase angle between voltage perturbations and current output and the impedance modulus, respectively, are plotted against frequency.

FIG. 4B is a Bode plot of the same impedance data as FIG. 4A. In FIG. 4B, frequency is plotted against the phase angle, θ, between voltage perturbations and current output, and against the impedance modulus, |Z|, respectively. As in FIG. 4A, changes in the relaxational behavior of electrochemical and transport processes that occur within the material as fatigue damage accumulates are reflected in the spectrally resolved impedance measurements.

Figure 5A:
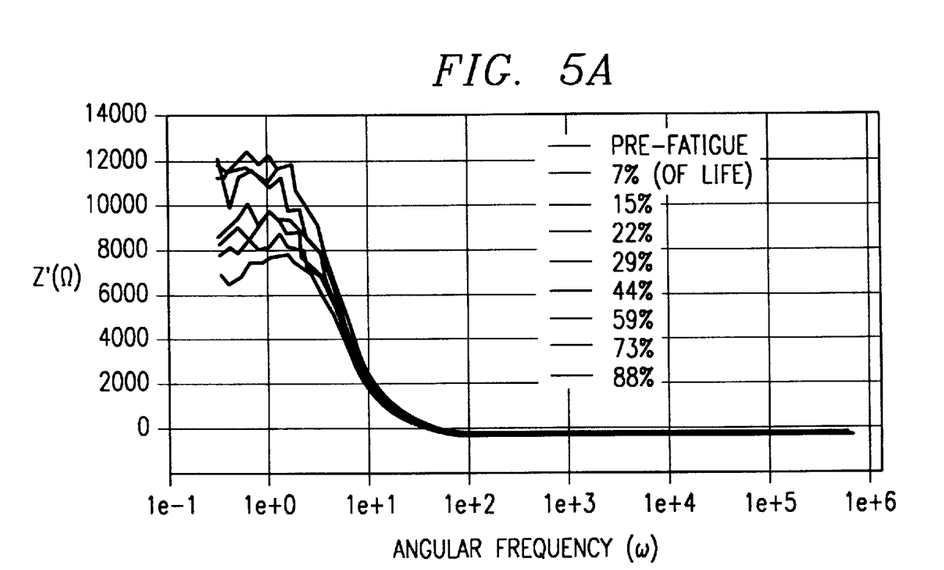
FIGS. 5A and 5B illustrate the impedance data of FIG. 4A is Debye dispersions.
Figure 5B:
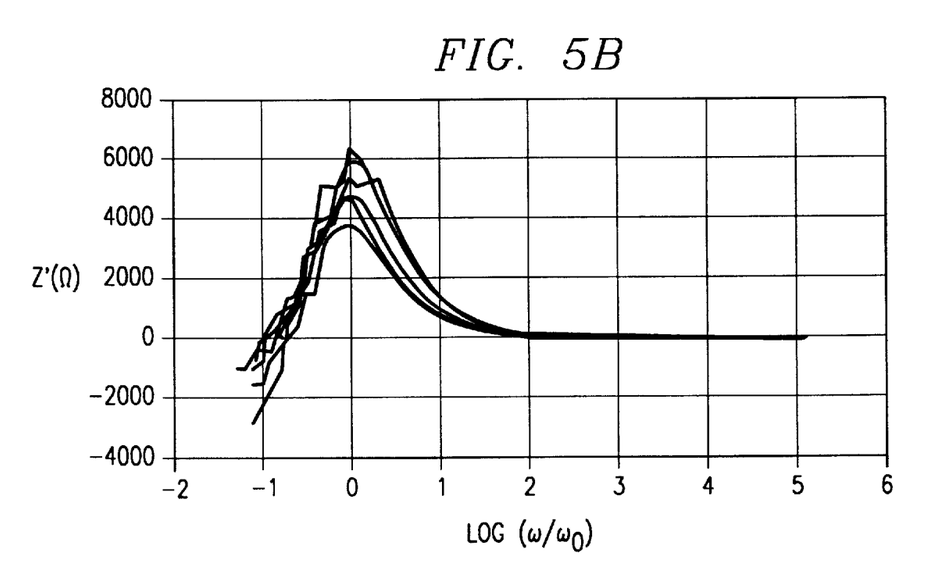

FIGS. 5A and 5B illustrate the impedance data as a Debye dispersion representation. FIG. 5A is a plot of the real component, Z', of the electrochemical impedance versus angular frequency, ω, of the applied perturbation. FIG. 5B is a plot of the imaginary component, Z", of the electrochemical impedance versus the log of the normalized angular frequency (normalized to the fundamental dispersion frequency). The characteristic shape and distribution of the imaginary component of the impedance measurements change around the fundamental frequency as a function of the state of fatigue damage.

Example 1 demonstrates that progressive states of fatigue damage within a metallic specimen that is maintained under OCP electrochemical conditions cause characteristic changes in the electrochemical impedance spectrum of the specimen. These changes may be observed when the electrochemical impedance is measured under zero applied load, that is, under mechanically static conditions.

EXAMPLE 2

Figure 6A:
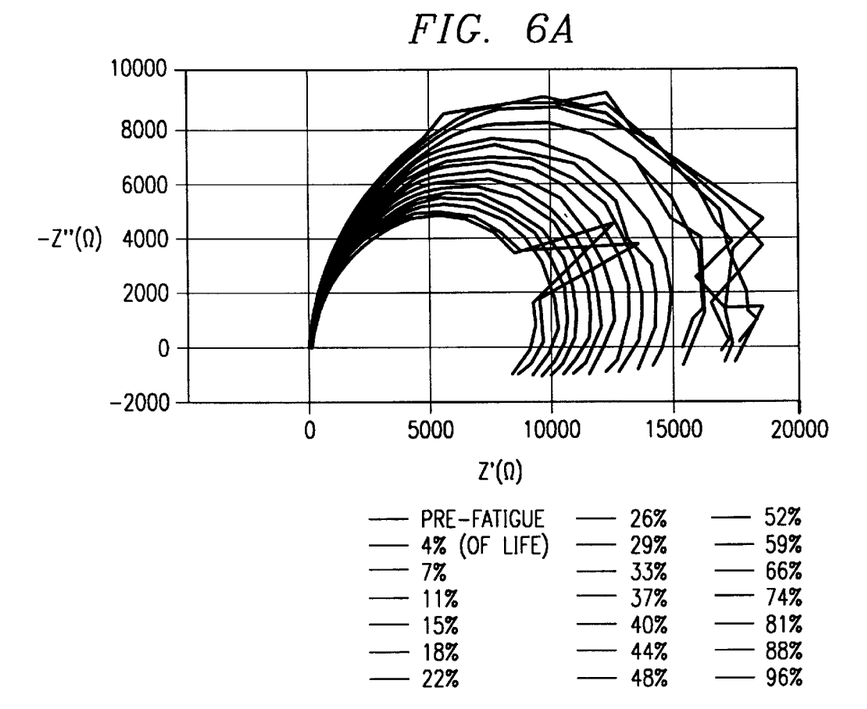
FIG. 6A is a Nyquist plot of the electrochemical impedance responses of an aircraft aluminum alloy during progressive states of mechanical fatigue damage, where the electrochemical transducer cell is held at a constant polarization potential.
Figure 6B:
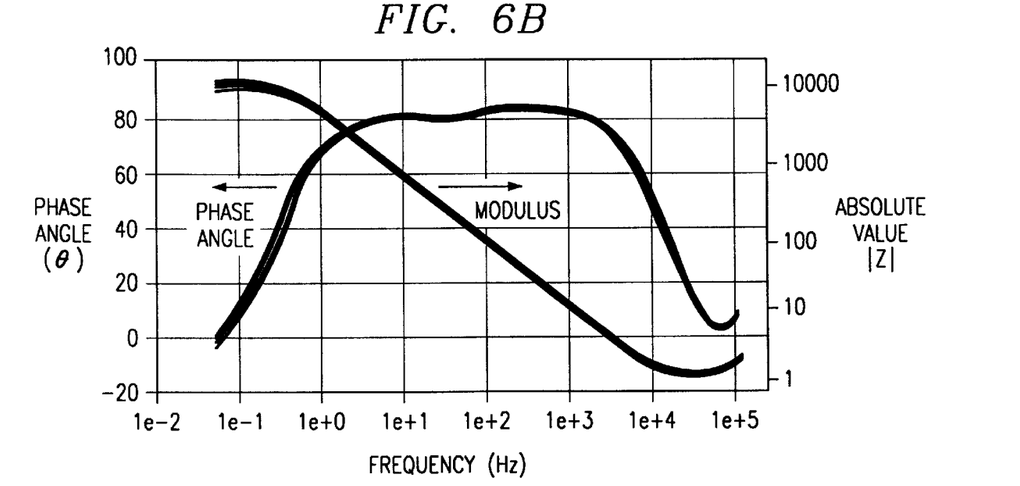
FIG. 6B is a Bode plot of the impedance data of FIG. 6A.

FIGS. 6A and 6B illustrate a second example (Example 2) of fatigue measurements in accordance with the invention. The same methods and apparatuses as described in connection with Example 1 were again used to probe the evolution of fatigue damage within rod-shaped tensile specimens of aircraft aluminum alloy (7075 AL). However, instead of being in an OCP condition, the specimen was subjected to a constant polarization potential of +300 mV versus the reference electrode during fatigue. The specimen was again intermittently interrogated during the cessation of fatigue using electrical voltage perturbations centered around a DC polarization potential.

FIGS. 6A and 6B are Nyquist and Bode plots similar to FIGS. 4A and 4B, and again show a monotonic contraction of the complex impedance arcs as the specimen accumulates progressively greater amounts of fatigue damage. Thus, Example 2 demonstrates that progressive states of fatigue damage within a metallic specimen that is maintained at a constant passive polarization potential cause characteristic changes in the electrochemical impedance spectrum of the specimen. These changes may be observed when the electrochemical impedance is measured under zero applied load, that is, under mechanically static conditions.

EXAMPLE 3

Figure 7A:
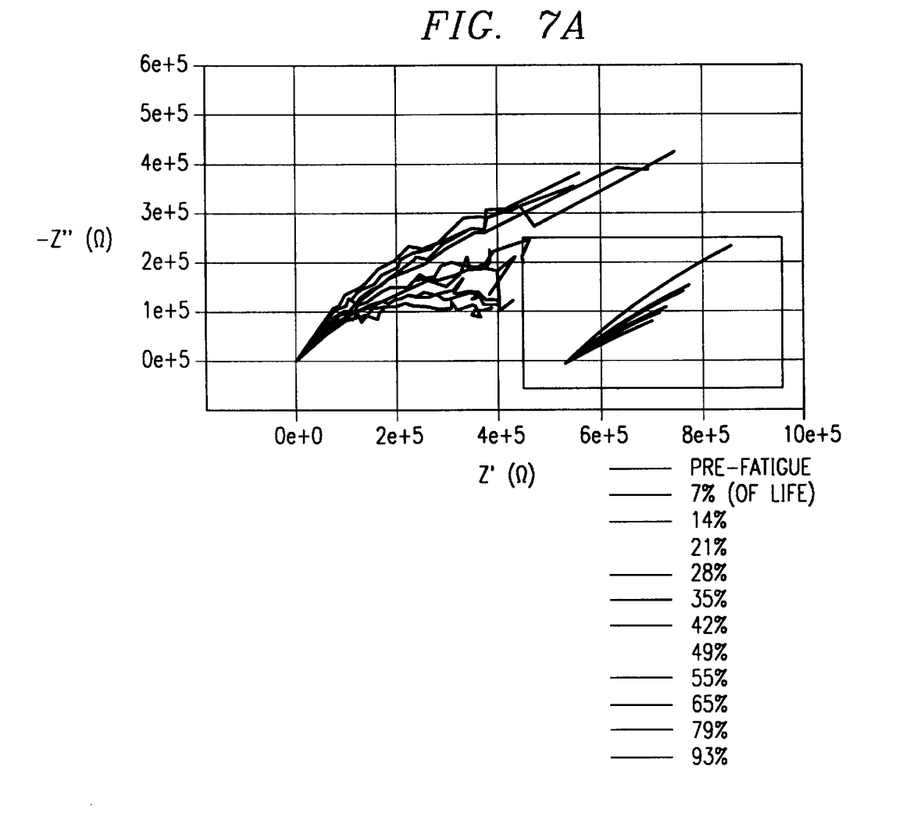
FIG. 7A is a Nyquist plot of the electrochemical impedance responses of a coated aircraft aluminum alloy during progressive states of mechanical fatigue damage, where the electrochemical transducer cell is held at a constant polarization potential.
Figure 7B:
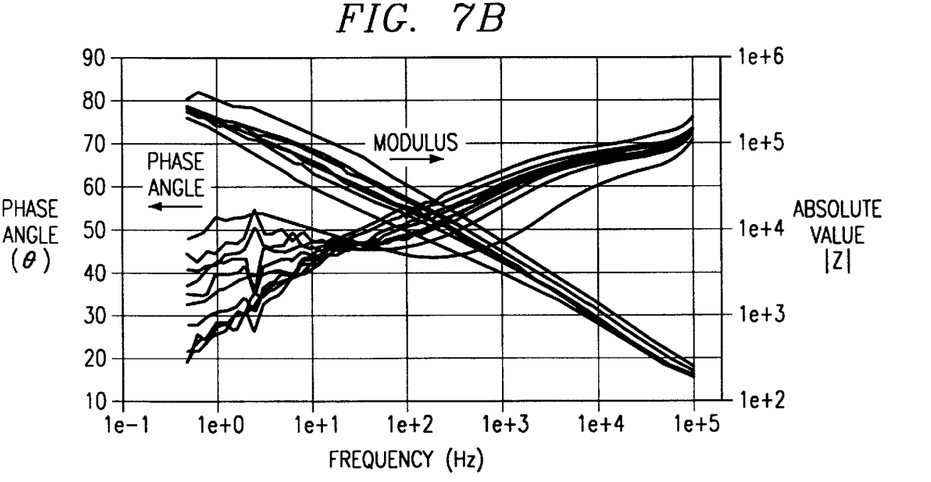
FIG. 7B is a Bode plot of the impedance data of FIG. 7A.

FIGS. 7A and 7B illustrate a third example (Example 3) of fatigue measurements in accordance with the invention. The same methods and apparatuses described above in connection with Examples 1 and 2 were used to probe the evolution of fatigue damage. However, Example 3 demonstrates the evolution of fatigue damage for a tensile specimen of aircraft aluminum alloy (7075 Al) that was chemically treated to remove surface oxides and other adherents, and subsequently spray painted with a primer coating. The chemical treatment and spray coating of the specimen was conducted in accordance with standard procedures established for the maintenance of military aircraft materials of this type. The chemical composition of the primer coating used in this example conformed to military aircraft specifications MIL P 23377G Type 1 Class C.

A constant polarization potential of +300 mV versus the reference electrode was applied to the specimen during fatigue as in Example 2. The specimen was again interrogated intermittently during the cessation of fatigue using electrical voltage perturbations centered around the DC polarization potential.

The results of these measurements are plotted in FIGS. 7A and 7B in the same fashion as was done for Examples 1 and 2 (FIGS. 4A, 4B, 6A, and 6B). Thus, FIGS. 7A and 7B are Nyquist and Bode plots of the electrochemical impedance response of primer-coated aircraft aluminum alloy (7075 Al) following progressive states of mechanical fatigue damage.

In Example 3, the impedance spectra change monotonically as a function of progressively greater amounts of fatigue damage. However, each spectrum contains two characteristic regions (i.e., time constants): one is associated with slow diffusion-limited processes that occur at the coating-substrate interface, which are realized at lower frequencies; and the other, which occurs at higher frequencies, is consistent with the dielectric behavior of the coating itself. The inset of FIG. 7A further exemplifies these monotonic changes in the region of higher frequencies.

Therefore, Example 3 demonstrates that progressive states of fatigue damage within a coated metallic substrate, as well as damage to the coating itself, cause characteristic changes in the electrochemical impedance spectrum of the coated specimen. These changes occur independently in two regions of the frequency spectrum, which can be discriminated by the methods of the invention.

Impedance Damage Parameters

Figure 8:
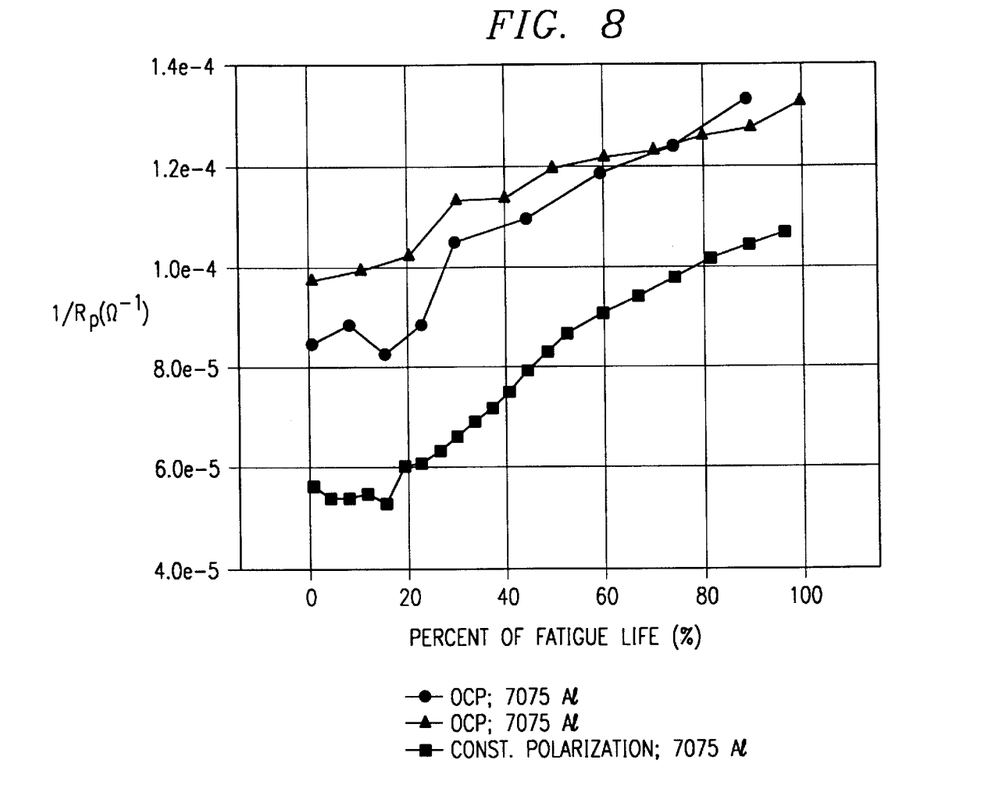
FIG. 8 illustrates a damage parameter, derived from electrochemical impedance measurements, that can be used to indicate implicitly the evolution of fatigue damage during the fatigue life of a material.

FIG. 8 illustrates a damage parameter, derived from electrochemical impedance measurements, that can be used to indicate implicitly the evolution of fatigue damage during the fatigue life of a material. As described in Examples 1 and 2 above, the electrochemical impedance responses of aircraft aluminum alloy (7075 Al) following progressive states of fatigue damage are used to demonstrate the mathematical derivation and correlation of this parameter. This parameter is defined as the implicit fatigue damage propagation, and designated symbolically as $1/R_p$. Two of the three plots are repetitions of Example 1 at open circuit potential (OCP), and the third plot is of Example 2 at constant polarization.

The implicit damage parameter ($1/R_p$) was determined from each electrochemical impedance arc of Examples 1 and 2 by fitting the Cole-Cole distribution model, which is mathematically defined above, to the impedance arc data obtained from the experimental measurements. The fitting parameters included the difference between the high and low limits of the real component of the impedance arc ($R_p = Z_{E,0} - Z_{E,\infty}$), the uncompensated resistance of the electrochemical transducer cell ($R_u = Z_{E,\infty}$), the relaxational time constant σ, and the distribution factor β, for nonlinear regression analysis. The best fit parameter value of $R_p$ was used to correlate the implicit fatigue damage propagation ($1/R_p$) with the fractional fatigue life of the specimen.

In the case of a multi component system, such as the coated specimen of Example 3, the damage state of each material component as a function of fatigue can be hypothetically defined and derived mathematically from the electrochemical impedance measurements. Hence, two independent damage parameters are relevant to the material system of Example 3:1) the implicit damage propagation of the coating, $1/R_{pore}$, which is related to changes in the resistance of pores, $R_{pore}$, and other defects within the coating; and 2) the implicit fatigue damage propagation of the substrate, $1/R_{ct}$, which takes into consideration the charge transfer resistance, $R_{ct}$, and diffusion limited processes associated with the electrochemical reactivity of the substrate at the interface between the coating and substrate.

For multi component systems, the implicit damage parameters, $1/R_{pore}$ and $1/R_{ct}$, may be deconvolved from the high- and low frequency regions (i.e., two time constants) of the impedance responses by fitting to the experimental curves of Example 3 (FIG. 7A) a model that combines the impedance response of the coating at the interface between the electrolyte and the coating, with that of the substrate at the interface between the coating and the substrate. The Cole-Cole distribution (Equation 3) may be used to mathematically describe the dielectric behavior of the coating, including pores and other defects within the coating that form an ensemble of dielectric interfaces. The impedance of the substrate in the interfacial region between the coating and the substrate is mathematically described by an expression that takes into consideration, in a general sense, the kinetics of charge transfer processes, and the transport (i.e., diffusion) of neutral or charged chemical species. The parameters or constants pertinent to an explicit description of the charge transfer and diffusion processes are combined into macroconstants to arrive at a generalized, hence, implicit form of the full expression. As a consequence of this parameterization in the implicit form of the model, the fitting parameters for treatment by nonlinear regression analysis may include: the difference between the high and low limits of the high frequency impedance arc, $R_{pore} = Z_{E,0}' - Z_{E,\infty}$; the uncompensated resistance of the electrochemical transducer cell, $R_u = Z_{E\infty}$; the relaxational time constant $\tau$; the distribution factor $\beta$, and charge transfer resistance, $R_{ct}$, associated with the low-frequency, constant-phase region of the impedance.

Figure 9:
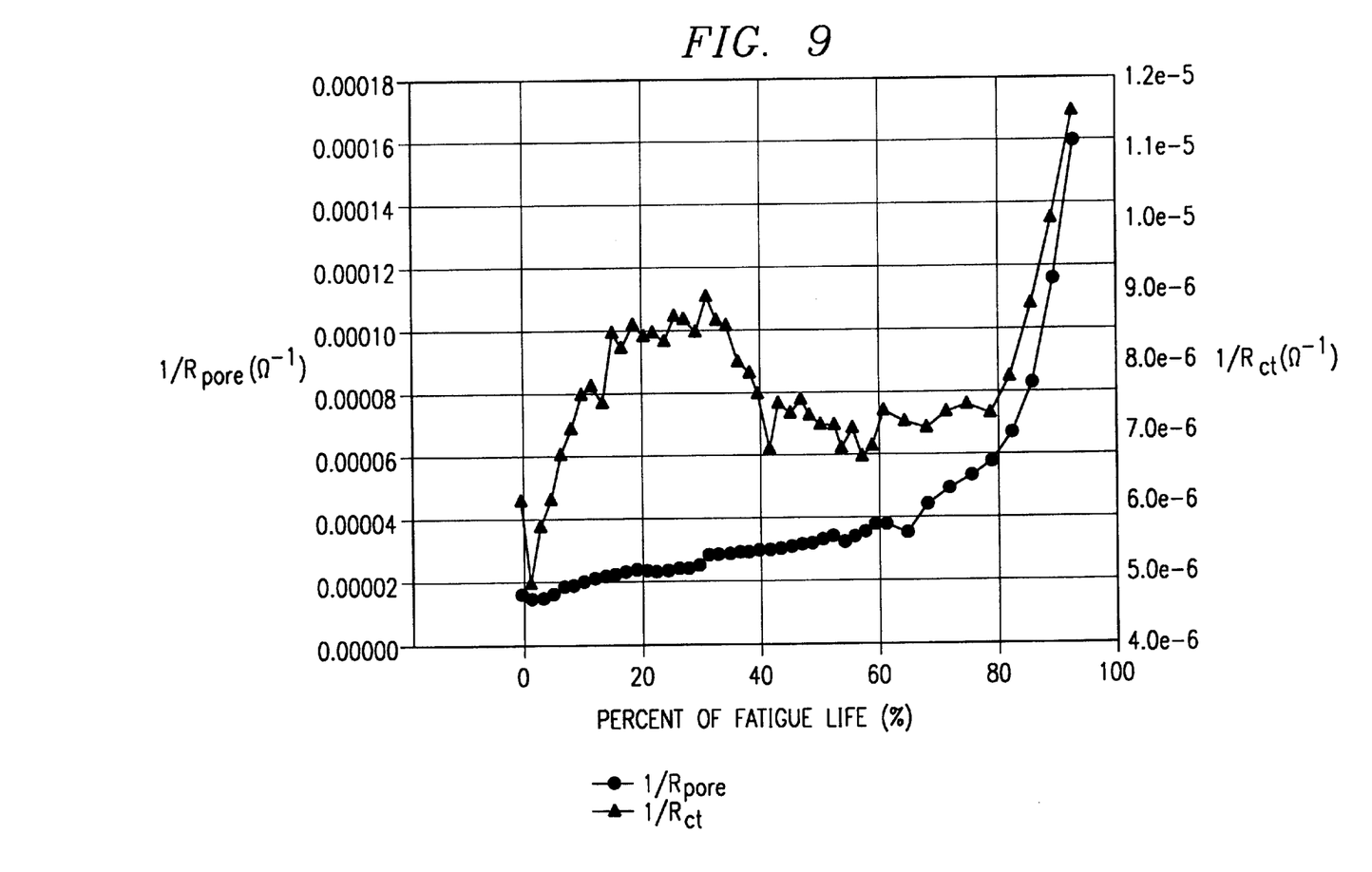
FIG. 9 illustrates two damage parameters, derived from electrochemical impedance measurements, that can be used to indicate implicitly the evolution of fatigue damage during the fatigue life of a coated material.

FIG. 9 represents the evolution of the implicit damage parameters for the coating, $1/R_{pore}$, and for the substrate, $1/R_{ct}$, as a function of fatigue life for Example 3. These implicit damage parameters, for each progressive state of fatigue damage, were deconvolved from the high- and low frequency regions of the impedance responses by fitting to the experimental impedance curves of FIG. 7A a generalized model which combines the Cole-Cole distribution (Equation 4) effect of the coating with the diffusion and charge transfer processes of the substrate. The best-fit parameter values of $R_{pore}$ and $R_{ct}$ were used to correlate the implicit damage propagation, $1/R_{pore}$, of the coating, and the implicit fatigue damage propagation of the aluminum substrate, $1/R_{ct}$, with the fractional fatigue life of the specimen.

In sum, the onset and evolution of fatigue damage within coated- and uncoated materials, such as aluminum alloy, is correlative with implicit damage parameters. These parameters can be numerically derived from the electrochemical impedance response of the material as measured under mechanically static conditions.

Electrochemical Transducer Array

FIGS. 10A–10D illustrate a transducer cell array 90, which may be used for impedance spectroscopy methods (EMIS and EIS) as well as for non-impedance electrochemical methods. For example, for EMIS or EIS methods, array 90 may be used instead of cell 10 in the system of FIG. 2. As explained below, array 90 may be used for electrochemical and electromechanical impedance imaging of coated or uncoated materials useful in the spatial characterization of the state of corrosion and fatigue damage of a substrate material, as well as the spatial integrity of a coating.

Array 90 provides data representing a spatial image of the impedance behavior of the material under test, rather than data representing only a single test region. For EMIS and EIS, spatially resolved images of fatigue damage based upon the frequency-dependent impedance response of the material can be obtained.

Figure 10A:
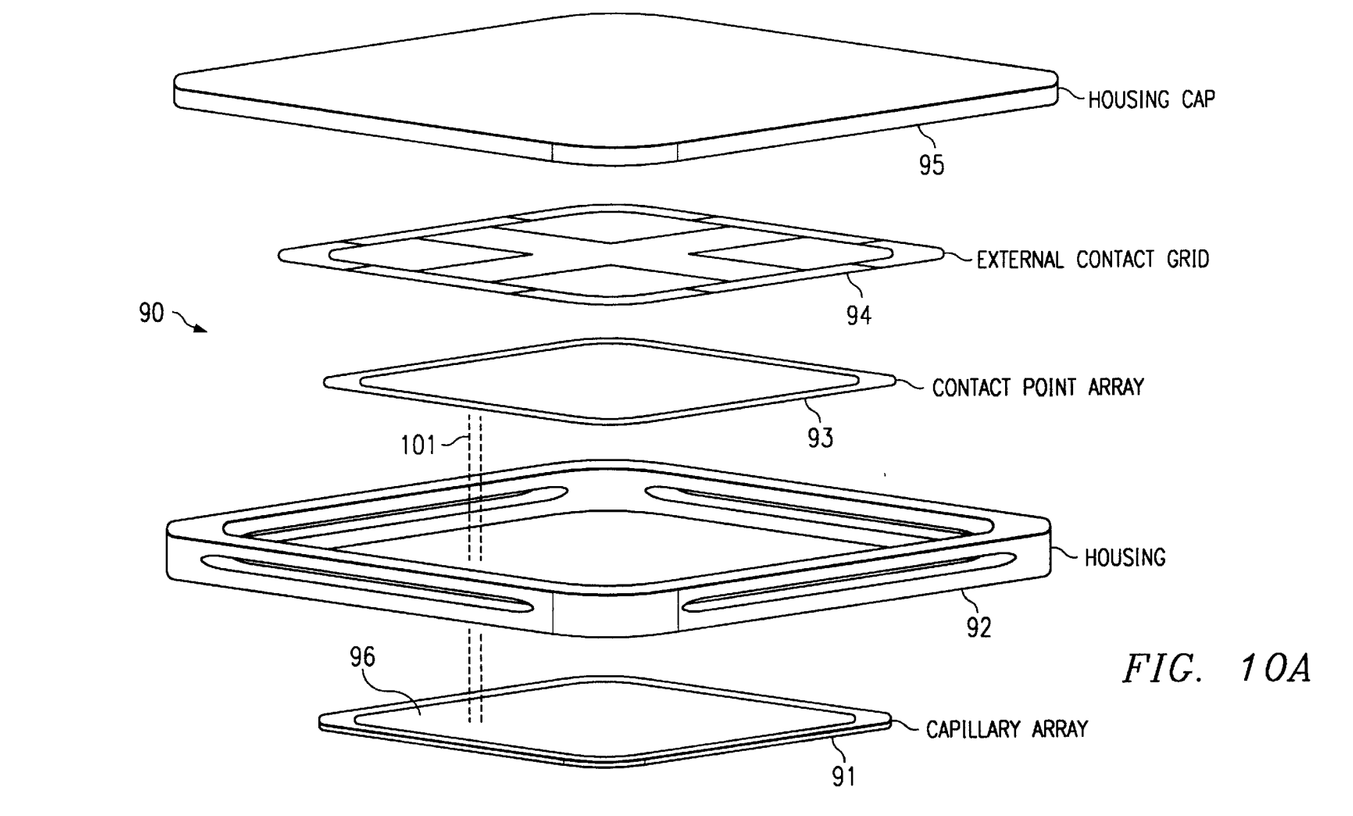
FIGS. 10A–10D illustrate a transducer cell array, which may be used for impedance spectroscopy methods (EMIS and EIS) as well as for non-impedance electrochemical methods.

FIG. 10A is an exploded view of array 90, showing its housing components 92 and 95 and active elements 91, 93, 94, and 96. Essentially, as indicated by the dotted lines, array 90 is an array of electrochemical transducer cell elements 101, contained in housing 92 and housing cap 95. Each cell element 101 operates on the same basic principle as a single electrochemical transducer cell 10.

Figure 10B:
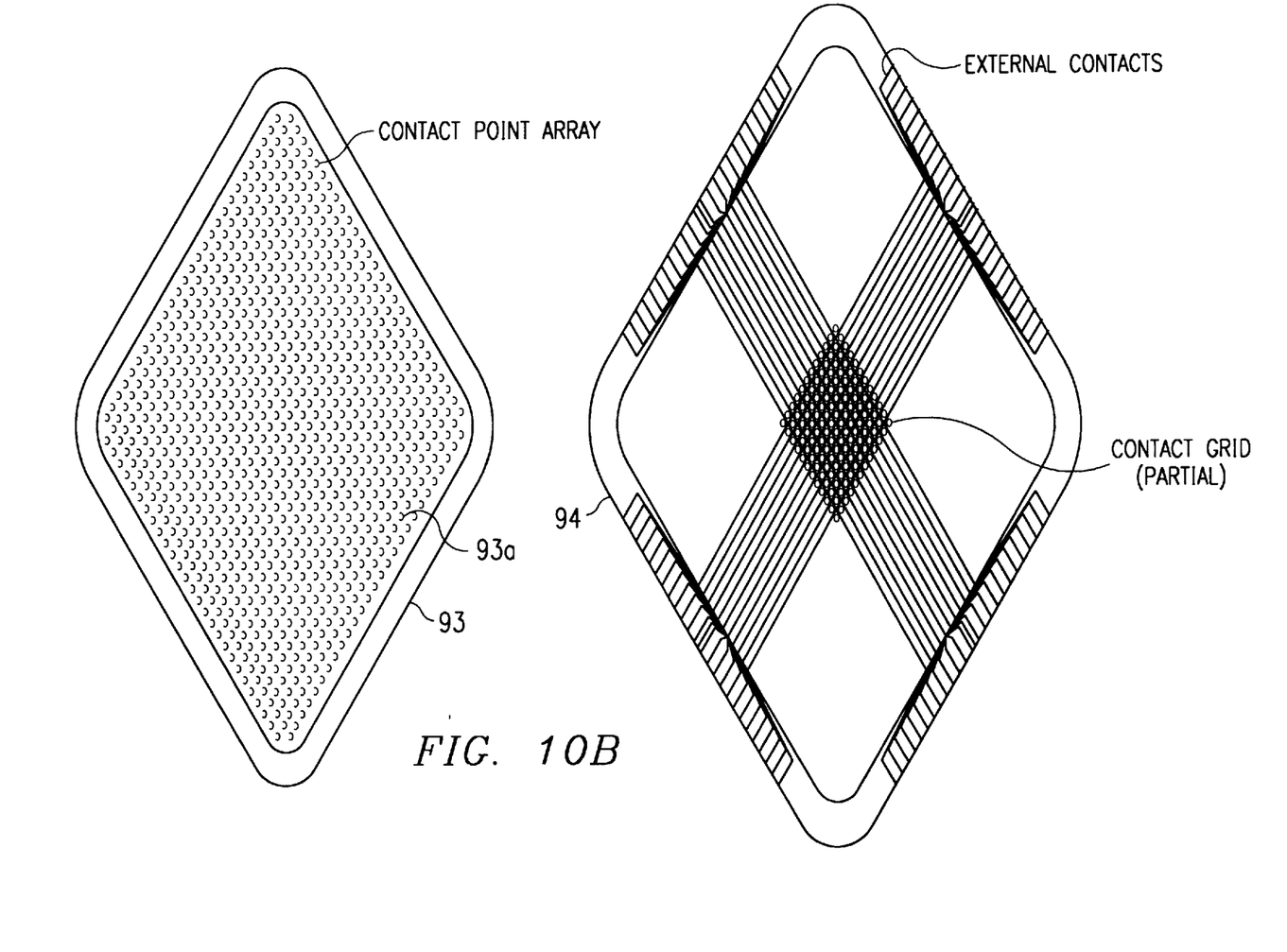

FIG. 10B is a more detailed view of the contact point array 93 and the contact grid 94. Each contact point 93a is an counter electrode, made from an inert metal such as platinum. Each contact point 93a is individually addressable, with contact grid 94 providing an electrical lead to each contact point 93a. The leads of the contact grid 94 are connected to a multiplexed version of the control/measurement unit 21 of FIG. 4. As explained below in connection with FIG. 11, contact point array 93 has an insulating layer that isolates the contact points 93a.

Figure 10C:
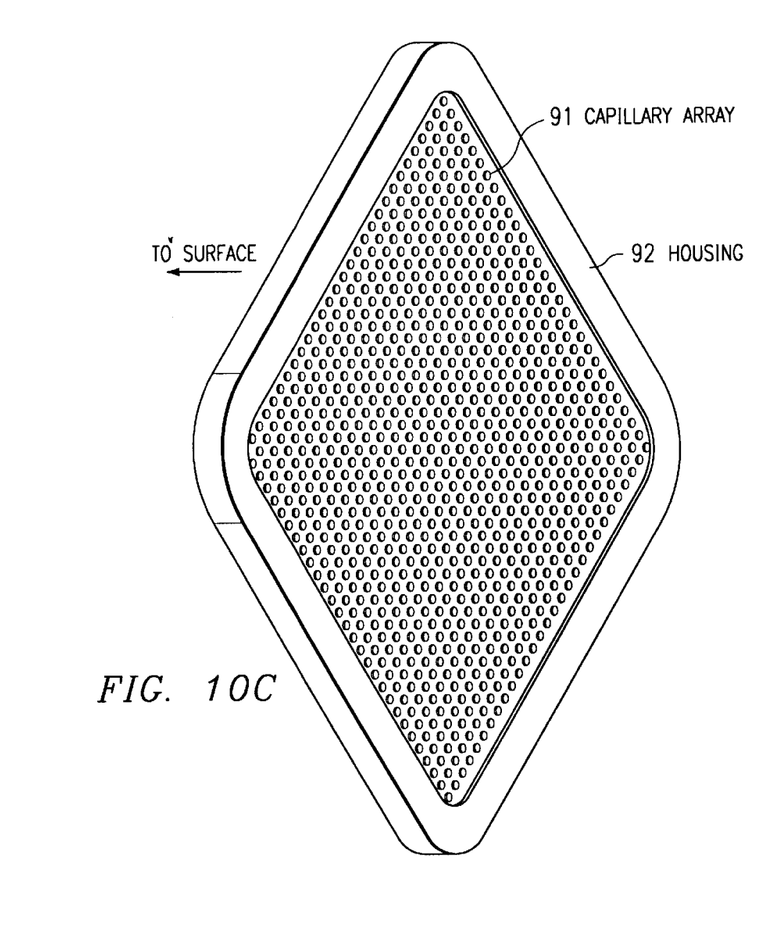
Figure 10D:
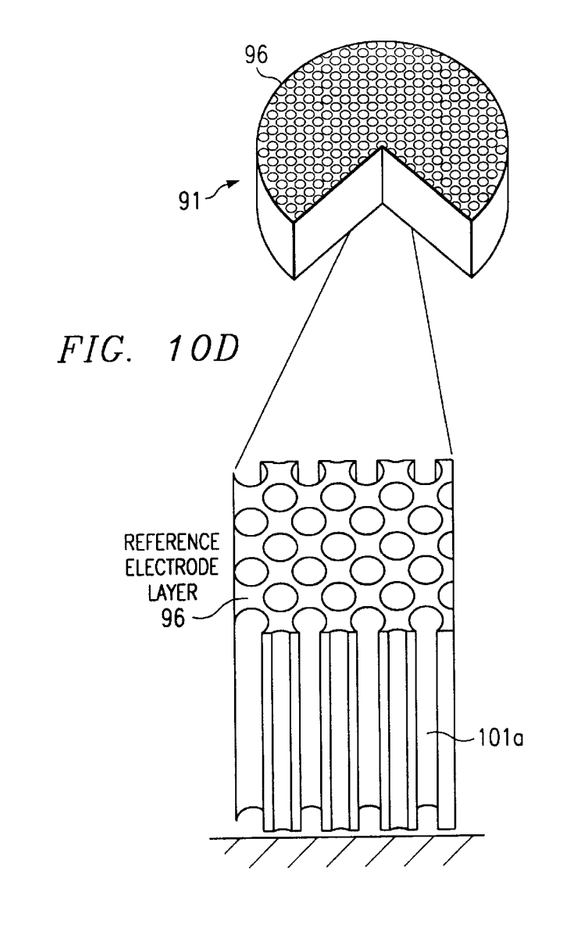

FIG. 10C is a more detailed view of the capillary array 91 and its housing 92. FIG. 10D is a sectional view of the capillary array 91. Each cell element 101 has its own capillary 91a, which is filled with an electrolyte. The bottom end of each capillary 91a is placed against the surface of the material under test. Capillary array 91 may be made from any insulating non porous material, such as glass, silicon, ceramic, or plastic. Suitable microchannel arrays are commercially available.

Capillary array 91 may be made sufficiently flexible so as to provide a uniform contact of all capillaries 91a. To this end, capillary array 91 might be made from a polymeric membrane material.

A reference electrode layer 96 is at the top surface of capillary array 91. As explained below in connection with FIG. 11, layer 96 forms a ring on the internal surface of each cell element 101. To form layer 96, the space between the capillaries 91a is coated with a suitable material, such as silver.

Figure 11:
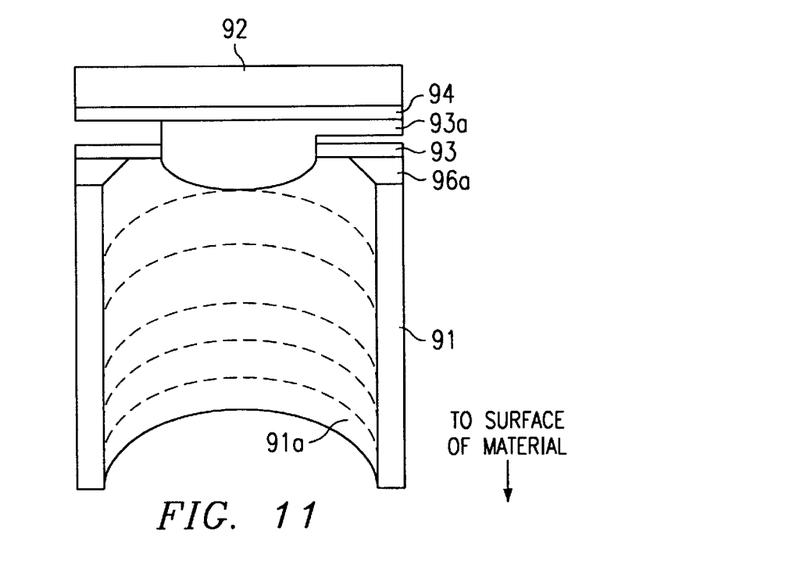
FIG. 11 illustrates a single cell element of the array of FIGS. 10A–10B.

FIG. 11 illustrates a single cell element 101 of the array 90. The components of array 90 form a sandwich-type arrangement with respect to the surface of the material under test (the working electrode). As stated above, the reference electrode layer 96 extends slightly into each capillary 91a to form a ring-shaped reference electrode 96a at the top edge of each cell element 101. This ring electrode 96a is electrically isolated from the contact points (counter electrode) 93a and the metal contact of grid 94 by the insulating layer of contact point array 93. The reference electrode 96a is also electrically isolated from the working electrode by the uncoated, non-conducting wall of the capillary element 91a.

The reference layer 96 forms a network of ring-shaped reference electrodes 96a connected in common with all cell elements 101. The metal contacts of the external contact grid 94, which make electrical contact with each contact point (counter electrode) 93a of the contact point array 93, run individually isolated paths along the external contact grid 94. Collectively, these paths form a grid of electrical leads that terminate at the outer edge of the array 90. The counter electrodes 93a are individually addressed via the multiplexed connection to control/measurement unit 21. Connection of the control/measurement unit 21 to the network of interconnected reference electrodes 96a is done at any single point, or multiple common points, along the edge of the reference electrode layer 96.

Prior to mating array 90 with the surface of a material to be interrogated, the electrolytic capillaries 91a of all cell elements 101 are "loaded" with electrolyte. The method of loading the electrolyte can be chosen from any one or more practices known to those in the art of capillary fluid dynamics, such as, but not limited to:

1. Centrifugation (centrifugal action), whereby a centrifuge apparatus, preferably equipped with a swinging bucket rotor, is used in conjunction with a container of suitable dimensions to restrain the array assembly, and to simultaneously force electrolyte into all cavities of the array. This may be accomplished by immersing the entire array assembly in electrolyte using the said container, and rotating the container at some frequency suitably chosen to impart an appropriate amount of centrifugal force onto the electrolyte and array assembly.

2. Sonication (sonicating action), whereby a conventional sonication device is used to exchange the air space contained within the empty cavities of the array, with electrolyte through sonic action.

3. Dielectrophoresis (dielectrophoretic mobility), whereby Maxwell forces will tend to elongate a polar fluid such as electrolyte, and induce the fluid to move into regions of an electric field. In this case, the array assembly itself and an opposing working electrode of planar geometry are used to exchange the air space, or other dielectric medium such as an organic fluid, contained within the cavities of the array, with electrolyte. Specifically, as a thin film of electrolyte is sandwiched between the capillary side of the array assembly and a planar working electrode, the counter electrodes of the array are simultaneously electrified at high frequency, and at some suitable potential relative to the working planar electrode. This will tend to induce dielectrophoretic mobility of the electrolyte into the cavities of the array.

Regardless of what method is chosen to load array 90 with electrolyte, the process should result in completely filling each capillary 91a such that the electrolyte is in contact with the counter electrode 93a of the point array 93, and with the ring 96a of the reference electrode layer 96. A meniscus of electrolyte should remain slightly protruded from the opening of each capillary 91a so that electrical contact can be made when mating array 90 with the surface of the material to be interrogated.

In sum, array 90 is an array of electrolytic volume cell elements 101, having spatial uniformity whose counter electrodes 93a can be of microscopic dimension and whose reference electrode 96 is common to all the volume elements. Each counter electrode 93a is individually addressable, thereby providing an array of impedance measurements. The total impedance response of the material, when the array volume elements are analyzed collectively, provides a spatially resolved, impedance spectral image of the array coverage.

The spatial resolution for the spectral image is predicated by the spatial discreteness of the array 90. For example, an array 90 assembled from a microchannel array can provide spatial resolutions of $50\mu m$ or better, with total array coverage ranging from 100 to 10,000 $mm^2$.

Other Embodiments

Although the present invention has been described in detail, it should be understood that various changes, substitutions, and alterations can be made hereto without departing from the spirit and scope of the invention as defined by the appended claims.

What is claimed is:

1. A transducer cell array for use in materials testing, comprising:

a capillary array having a number of capillary elements open at each end, such that each capillary element has an open top end and an open bottom end;

an electrically conductive reference electrode layer at the upper surface of said capillary array, said reference electrode layer extending down into a least a portion of each said capillary element thereby forming a reference electrode for each capillary element;

a contact point array above the reference electrode layer, having a number of electrically conductive contact points, each of said contact points forming a counter electrode for a corresponding capillary element; and a contact grid having a number of electrical leads, one lead corresponding to each counter electrode such that each counter electrode is individually addressable.

2. The array of claim 1, wherein said contact point array has an insulating layer separating each said contact point from its corresponding reference electrode.

3. The array of claim 1, wherein said capillary array is made from a flexible material.

4. The array of claim 1, wherein said reference layer forms a ring at the upper portion of said top open end of each said capillary element.

5. The array of claim 1, further comprising means for connecting said reference layer to a common electrical potential.

6. The array of claim 1, wherein the capillary elements are made from a non-conductive material such that each reference electrode is electrically isolated from the surface of the material.

7. The array of claim 1, wherein the capillary elements are at least partially spaced from each other and wherein the reference electrode layer covers the spaces between the capillary elements and has a number of apertures, each of the apertures corresponding to a top open end of each capillary element.

8. The array of claim 1, wherein each capillary element is round.

\* \* \* \* \*